United States Patent [19]
Dearnaley

[11] Patent Number: 5,945,153
[45] Date of Patent: Aug. 31, 1999

[54] NON-IRRITATING ANTIMICROBIAL COATING FOR MEDICAL IMPLANTS AND A PROCESS FOR PREPARING SAME

[75] Inventor: Geoffrey Dearnaley, San Antonio, Tex.

[73] Assignee: Southwest Research Institute, San Antonio, Tex.

[21] Appl. No.: 08/902,488

[22] Filed: Jul. 29, 1997

Related U.S. Application Data

[63] Continuation of application No. 08/635,395, Apr. 25, 1996, which is a continuation-in-part of application No. 08/483,741, Jun. 7, 1995, abandoned, which is a continuation-in-part of application No. 08/273,397, Jul. 11, 1994, abandoned.

[51] Int. Cl.$^6$ .............................. B05D 3/00; A61L 27/00; C23C 14/00; C23C 16/00
[52] U.S. Cl. ...................... 427/2.12; 427/2.24; 427/2.26; 427/525; 427/527; 427/530; 427/528; 427/531; 427/566; 427/533; 427/249; 427/250; 427/255.2
[58] Field of Search ................................... 427/2.1, 2.12, 427/2.24, 2.26, 523, 524, 525, 527, 528, 530, 531, 533, 566, 581, 595, 249, 250, 255.2; 204/192.14, 192.15, 192.16, 192.17

[56] References Cited

U.S. PATENT DOCUMENTS

| | | |
|---|---|---|
| 3,119,707 | 1/1964 | Christy . |
| 3,605,123 | 9/1971 | Hahn . |

(List continued on next page.)

FOREIGN PATENT DOCUMENTS

| | | |
|---|---|---|
| 0 548 788 A2 | 12/1991 | European Pat. Off. . |
| 62-196371 | 2/1986 | Japan . |
| 62-202897 | 2/1986 | Japan . |

OTHER PUBLICATIONS

Gao et al., "Surface Treatment of ultra high molecular weight polyethylene to enhance adhesion and conductivity properties," 33 Polymer 19 (1992), 6 pp. No month.

Bodo et al., "Adhesion of evaporated titanium to polyethylene: Effects of ion bombardment pretreatment," J. Vac. Sci. Technol. A2(4) (1984), pp. 1498–1502. Oct.–Dec.

Davidson et al., "Surface Modification Issues for Orthopaedic Implant Bearing Surfaces," Surface Modification Technologies V (1992), pp. 1–14. no month.

Bedell et al., "Diamond–like carbon from the ion–beam decomposition of polyphenyl ether," Applications of Diamond Films & Related Materials, (1991), pp. 833–838. No month.

Jones et al., "Stress and Microstructure of Diamond–Like Carbon From Ion–Beam Decomposition of Hydrocarbon Precursors," paper presented 2nd European Conference on Diamond, Diamond–like and Related Coatings, Nice, France (1991), pp. 1–18. Sep.

Dumbleton, "The Clinical Significance of Wear in Total Hip and Knee Prostheses," Jnl of Biomaterials Applications, vol. 3 (1988), pp. 7–32. Jul.

Lankford et al., "Adherence of diamondlike carbon coatings on total joint substrate materials," Nuclear Instruments and Methods in Physics Research B80/81 (1993), pp. 1441–1445. No month.

Butter et al., "Diamond–Like Carbon for Biomedical Applications," Applied Diamond Conference (1995), pp. 683, 688, 690. Aug.

Dearnaley et al., "Bioapplications of Diamond–Like Carbon Coatings," paper presented 4th World Biomaterials Congress (1992), 9 pp. Apr.

Legg, "Surface Engineering with Ion–Assisted Coatings," Nuclear Instruments and Methods in Physics Research B24/25 (1987), pp. 565–567. No month.

(List continued on next page.)

*Primary Examiner*—Marianne Padgett
*Attorney, Agent, or Firm*—Madan & Morris, PLLC

[57] ABSTRACT

The present invention provides a process of forming an antimicrobial coating on a surface of a medical implant, the coating comprising an antimicrobially effective amount of antimicrobial metal atoms incorporated into a coating of amorphous carbonaceous material.

24 Claims, 1 Drawing Sheet

U.S. PATENT DOCUMENTS

| | | |
|---|---|---|
| 3,707,006 | 12/1972 | Bokros et al. . |
| 3,906,550 | 9/1975 | Rostoker et al. . |
| 4,241,355 | 12/1980 | Bloom et al. . |
| 4,362,681 | 12/1982 | Spector et al. . |
| 4,410,611 | 10/1983 | MacIver . |
| 4,452,827 | 6/1984 | Kolev et al. . |
| 4,474,827 | 10/1984 | Ferralli . |
| 4,486,286 | 12/1984 | Lewin et al. . |
| 4,495,044 | 1/1985 | Banks . |
| 4,554,208 | 11/1985 | MacIver et al. . |
| 4,606,354 | 8/1986 | Jacob . |
| 4,615,705 | 10/1986 | Scales et al. . |
| 4,634,600 | 1/1987 | Shimizu et al. . |
| 4,647,494 | 3/1987 | Meyerson et al. . |
| 4,698,236 | 10/1987 | Kellogg et al. . |
| 4,713,258 | 12/1987 | Umemura . |
| 4,722,870 | 2/1988 | White . |
| 4,725,345 | 2/1988 | Sakamoto et al. . |
| 4,743,493 | 5/1988 | Sioshansi et al. . |
| 4,746,538 | 5/1988 | Mackowski . |
| 4,756,964 | 7/1988 | Kincaid et al. . |
| 4,772,513 | 9/1988 | Sakamoto et al. . |
| 4,795,656 | 1/1989 | Mizoguchi et al. . |
| 4,822,466 | 4/1989 | Rabalais et al. . |
| 4,877,677 | 10/1989 | Hirochi et al. . |
| 4,906,466 | 3/1990 | Edwards et al. . |
| 4,957,771 | 9/1990 | Enloe . |
| 4,961,958 | 10/1990 | Desphandey et al. . |
| 4,981,071 | 1/1991 | Enke . |
| 4,988,421 | 1/1991 | Drawl et al. . |
| 4,992,298 | 2/1991 | Deutchman et al. . |
| 5,009,923 | 4/1991 | Ogata et al. . |
| 5,028,451 | 7/1991 | Ito et al. . |
| 5,064,682 | 11/1991 | Kiyama et al. . |
| 5,068,020 | 11/1991 | Chu et al. . |
| 5,084,151 | 1/1992 | Vallana et al. . |
| 5,106,533 | 4/1992 | Hendrickson et al. . |
| 5,126,163 | 6/1992 | Chan . |
| 5,133,757 | 7/1992 | Sioshansi et al. . |
| 5,135,808 | 8/1992 | Kimock et al. . |
| 5,139,592 | 8/1992 | Debe . |
| 5,169,597 | 12/1992 | Davidson et al. . |
| 5,192,523 | 3/1993 | Wu et al. . |
| 5,234,724 | 8/1993 | Schmidt . |
| 5,252,174 | 10/1993 | Deguchi et al. . |
| 5,266,398 | 11/1993 | Hioki et al. . |
| 5,270,252 | 12/1993 | Papanicolaou . |
| 5,340,850 | 8/1994 | Shimasne ............................. 427/529 |
| 5,352,493 | 10/1994 | Dorfman et al. ..................... 427/530 |
| 5,391,407 | 2/1995 | Dearnaley . |
| 5,425,777 | 6/1995 | Sarkisian et al. . |
| 5,474,797 | 12/1995 | Shioshansi et al. ................... 427/531 |
| 5,477,865 | 12/1995 | Davidson .............................. 128/772 |
| 5,516,884 | 5/1996 | Bianconi ............................... 528/397 |

OTHER PUBLICATIONS

Dearnaley, "Materials Science Aspects of Ion Beam Technology," Surface Engineering, vol. 7, No. 2 (1991), pp. 127–136. No month.

Evans, et al., "Diamond–Like Carbon Applied to Bioengineering Materials," Medical Device Technology, (1991), pp. 26–29. May.

Agrawal, et al., "The Effects of Diamond–like–Carbon Coatings on the Friction and Wear of Enhanced UHMW-PE–Metal Couples," 19th Annual Meeting of Society for Biomaterials, (1993), p. 10. May.

Browne, Malcolm W., "Diamond coating may be future of tool manufacture," San Antonio Express News, (Apr. 1, 1996), 1 page.

NON-IRRITATING ANTIMICROBIAL COATING FOR MEDICAL IMPLANTS AND A PROCESS FOR PREPARING SAME

CROSS-REFERENCE TO RELATED APPLICATIONS

This application is a continuation of application Ser. No. 08/635,395 filed Apr. 25, 1996, which is a continuation-in-part of application Ser. No. 08/483,741, filed on Jun. 7, 1995, now abandoned, which is a continuation-in-part of application Ser. No. 08/273,397, filed on Jul. 11, 1994, now abandoned.

FIELD OF THE INVENTION

The present invention provides medical implants having a noncrystalline, high hardness, low friction, antimicrobial coating which is relatively well-tolerated by the body, and a process for preparing such coatings.

BACKGROUND OF THE INVENTION

A common cause of failure of implanted biomedical devices is infection. The attachment of bacteria to medical implants and in-dwelling catheters, and the proliferation of such bacteria, is a major cause of infection during or after the implantation process. Treating an implant with antibiotics has not proven very effective to combat infections, and has sometimes resulted in the development of resistant strains of bacteria.

Silver coatings are effective to combat infections; however, silver coatings tend to cause tissue irritation, largely due to excessively rapid release of the silver into the surrounding tissues.

An antimicrobial coating for a medical implant is needed which has hardness and low friction properties, and that will result in a slow, long-term release of antimicrobial metal atoms into the body in order to prevent infection.

SUMMARY OF THE INVENTION

The present invention provides a process of forming an antimicrobial coating on the surface of a medical implant comprising the steps of: placing the medical implant in a vacuum chamber evacuated to a pressure of less than about $10^{-5}$ torr; depositing metal atoms, preferably silver atoms, onto the surface of the medical implant in an amount sufficient to impart antimicrobial protection to the medical implant; directing a vaporized stream of hydrocarbon precursor molecules toward the surface of the medical implant under temperature conditions sufficient to condense the hydrocarbon precursor molecules onto the surface of the implant, thereby forming a precursor film; and, bombarding the precursor film with an energetic beam of ions at a first energy, a first rate of ion arrival, and for a first amount of time sufficient to form on said surface a non-crystalline, amorphous carbonaceous coating containing an antimicrobially effective amount of said metal atoms. In an alternate embodiment, the metal is deposited onto the surface of the implant via an organo-metallic compound, which is used as the precursor material for the carbonaceous coating.

DETAILED DESCRIPTION OF THE INVENTION

Figure 1:
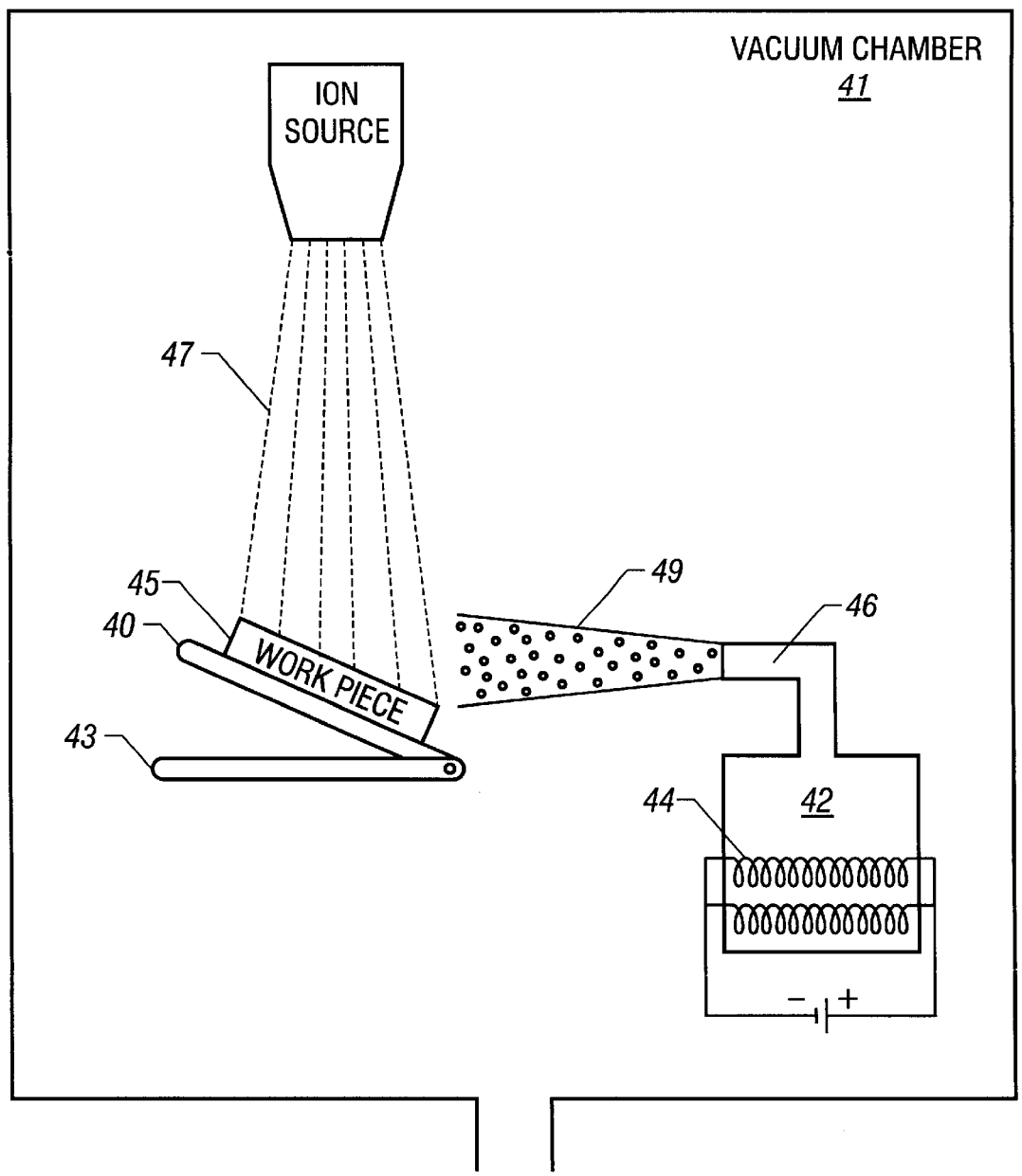
FIG. 1 is an apparatus for use in practicing the present invention.

According to the present invention, a medical implant is provided with an amorphous, diamond-like carbon (DLC) coating in which antimicrobial metal atoms, preferably silver atoms, are disposed. The DLC coating prevents rapid release of the metal atoms into the surrounding tissues, thereby avoiding tissue irritation.

DLC is a biocompatible, amorphous carbon material that can be used to coat a variety of materials. DLC may be used to coat components made from biomaterials that include, but are not limited to, the following: substantially any metal alloy; various polymers, including but not limited to high density polyethylene, ultra-high molecular weight polyethylene, various polyetheretherketones; and, and various ceramic materials. Materials that have been approved by the FDA for use in medical implants are preferred materials for use in the present invention.

The DLC coating of the present invention is formed using ion beam assisted deposition. The metal atoms may be deposited onto the surface of the implant in several different ways. In a first method, a vaporized stream of the metal atoms may be directed toward the surface to be treated via a sputtering process employing an ion beam of the metal atoms. In this embodiment, the rate of arrival of the metal ions may be controlled directly by controlling the intensity of the ion beam measured as an electrical current to the sputtering electrode. In other methods, the vaporized stream of the metal atoms may be generated from a pool of metal in an electron beam heated hearth, or from a pool of molten metal contained in a resistively heated evaporator. The vaporization of metal atoms generally takes place at a temperature of approximately 1200° C. (2192° F.), and the rate of arrival of the metal atoms may be controlled by controlling the thermal power delivered to the hearth or the evaporator. In another method, described in more detail below, the metal atoms are provided in an organo-metallic compound that is used as the hydrocarbon precursor for the DLC coating.

In a first type of process, metal atoms are deposited onto the surface of the implant during an initial, separate step. After the metal ions have been deposited, a vaporized stream of hydrocarbon precursor molecules is directed toward the surface of the implant under temperature conditions that cause the hydrogen precursor to condense onto the surface of the implant.

In a preferred embodiment, the rate of arrival of the metal atoms and the hydrocarbon precursor should be calibrated so that about 1 atom of metal is deposited for about every 10 molecules of hydrocarbon precursor. The rate of arrival of these atoms can be controlled by monitoring the thickness of the coating using standard methods, e.g., by measuring the change in resonant frequency of a quartz crystal oscillator positioned near the substrate being coated. The rate of arrival also may be measured after the deposition process is complete using an analytical technique known as Rutherford Backscattering Spectroscopy (RBS), a known technique described in THE HANDBOOK OF MODERN ION BEAM MATERIALS ANALYSIS 37–82 (Joseph R. Tesmer and Michael Nastasi, eds., The Materials Research Society, Pittsburgh Pa. 1995), incorporated herein by reference.

Suitable hydrocarbon precursor materials for the DLC coating include carbon-based diffusion pump materials which have a low vapor pressure and can be vaporized stably at room temperature. Examples of such materials include, but are not necessarily limited to: polyphenyl ether; elcosyl naphthalene; i-diamyl phthalate; i-diamyl sebacate; chlorinated hydrocarbons; n-dibutyl phthalate; n-dibutyl sebacate; 2-ethyl hexyl sebacate; 2-ethyl hexyl phthalate; di-2-ethyl-hexyl sebacate; tri-m-cresyl phosphate; tri-p-cresyl phosphate; dibenzyl sebacate. Preferred diffusion pump fluids include, but are not necessarily limited to, polyphenyl ether and elcosyl naphthalene. A most preferred hydrocarbon precursor is polyphenyl ether. Polydimethyl siloxane, pentaphenyltrimethyl siloxane, and other silicon containing diffusion pump fluids will work in the present invention, but are not preferred because the silicon contained in these diffusion pump fluids would be a component of the outer coating of the implant. Other suitable hydrocarbon precursors contain carbon and other constituent elements, such as oxygen, nitrogen, or fluorine.

The hydrocarbon precursor may be vaporized and condensed onto the surface of the component using known means. Generally, the precursor is placed in a reservoir, heated to between about 150° C.–170° C. (302° F.–338° F.), and directed onto the component, for example, using a right angled nozzle. Either substantially simultaneously or sequentially, the component should be bombarded, either in a continuous or interrupted fashion, with an energetic beam of ions. A preferred ion source is nitrogen. Other suitable ions include, but are not necessarily limited to, argon, hydrogen, silicon, methane, helium, or neon. The ion beam should have an energy between about 500 eV to 100 keV, preferably about 10 keV. The energy of bombardment must be sufficient to ionize the constituent molecules in the precursor film, and to rupture the bonds between hydrogen and other atoms, thereby releasing the hydrogen into the surrounding vacuum to be pumped away.

The "ion arrival ratio" should be controlled in relation to the rate of arrival of the hydrocarbon precursor molecules. The "ion arrival ratio" is defined as the ratio of each arriving ion to the number of precursor molecules present at the surface of the component. The ion arrival ratio preferably should be at least 1 ion for every molecule of hydrocarbon precursor. This process should require about one ion for every 100 atoms in the final product coating; however, the required ion-to-atom ratio will vary according to the mass and energy of the ion species. Typically, 100 eV must be deposited for each carbon atom in the coating.

The function of this ion bombardment step is to rupture at least about 80% of the carbon-hydrogen bonds in the precursor, resulting in the formation of a noncrystalline coating of amorphous carbon. The energy dissipated by the energetic ion bombardment during ion beam assisted deposition is in the form of inelastic electronic excitations equivalent to at least about 100 eV for each carbon atom within the deposited coating. This energy dissipation strongly enhances adhesion of the DLC coating by rupturing and subsequently reforming interatomic bonds across the interfaces. Persons of ordinary skill in the art will recognize how to achieve the correct linear energy of transfer in the ionizing process.

As mentioned, the last two steps of the present invention (deposition of hydrocarbon precursor and ion bombardment) may be performed either sequentially or substantially simultaneously. As shown in FIG. 1, workpiece 45 may be mounted on rotatable surface 40 which can be oriented such that workpiece 35 is exposed simultaneously to ion beam 47 and vapor stream 49. Alternatively, if mounting surface 40 is rotated at a right angle to base 43, workpiece 45 would be exposed only to vapor stream 49. Alternately, base 43 can be raised or nozzle 46 can be turned to face another direction, such that the surface of workpiece 45 is only exposed to ion beam 47.

The deposition of metal atoms, the deposition of hydrocarbon precursor, and the bombardment with an energetic ion beam can be repeated as many times as desired to achieve a uniform coating of a desired thickness on the surface to be treated. In a preferred embodiment, these steps are repeated as many times as are required to achieve a coating with a thickness of between about 1–5 microns.

In an alternate embodiment of the present invention, a vaporized stream of a metallo-organic compound is directed toward the surface to be treated under conditions that cause the metallo-organic compound to condense onto the surface of the implant, resulting in a film of metallo-organic compound. The term "metallo-organic compound" is defined as containing either silver or gold as the metallic component. In a preferred embodiment, the metallo-organic compound is silver phthalocyanine. After the metallo-organic compound is condensed onto the surface of the component, the surface is bombarded with an energetic ion beam, as described above.

Many modifications and variations may be made in the embodiments described herein and depicted in the accompanying drawings without departing from the concept of the present invention. Accordingly, it is clearly understood that the embodiments described and illustrated herein are illustrative only and are not intended as a limitation upon the scope of the present invention.

I claim:

1. A process of forming an antimicrobial coating on a surface of a biomaterial comprising:

exposing said surface of said biomaterial to a vacuum sufficient to permit a vaporized stream of a carbon-based diffusion pump fluid to condense onto said surface;

depositing onto said surface metal atoms selected from the group consisting of silver, gold, and a combination thereof;

directing onto said surface a vaporized stream of said carbon-based diffusion pump fluid under temperature conditions sufficient to condense said fluid onto said surface, thereby forming a diamond-like carbon precursor film;

bombarding said diamond-like carbon precursor film with an energetic beam of ions under conditions effective to form on said surface an amorphous diamond-like carbon coating comprising a dispersion of said metal atoms;

wherein said dispersion of said metal atoms in said diamond-like carbon coating is effective to provide gradual, controlled release of said metal from said on coating at a rate effective to impart antimicrobial protection, but insufficient to irritate tissue which comes into contact with said surface.

2. The process of claim 1 wherein said process is repeated until said diamond-like carbon coating has a thickness of between about 1–5 microns.

3. The process of claim 1 wherein said energy is about 10 keV.

4. The process of claim 2 wherein said energy is about 10 keV.

5. The process of claim 1 wherein said metal atoms are silver atoms.

6. The process of claim 2 wherein said metal atoms are silver atoms.

7. The process of claim 1 wherein said amount of said metal atoms is about 10 metal atoms for every molecule of said carbon-based diffusion pump fluid.

8. The process of claim 4 wherein said amount of said metal atoms is about 10 metal atoms for every molecule of said carbon-based diffusion pump fluid.

9. The process of claim 1 wherein said depositing said metal atoms comprises sputtering said metal atoms onto said surface.

10. The process of claim 1 wherein said depositing said metal atoms comprises sputtering said metal atoms onto said surface.

11. The process of claim 1 wherein said carbon-based diffusion pump fluid comprises elements selected from the group consisting of oxygen, nitrogen, fluorine, and combinations thereof.

12. The method of claim 1 wherein said vacuum comprises a vacuum chamber evacuated to a pressure of about $10^{-5}$ torr or less.

13. A process of forming an antimicrobial coating on a surface of a medical implant comprising:

exposing said implant to a vacuum sufficient to permit a vaporized stream comprising polyphenyl ether to condense onto said surface of said implant;

depositing metal atoms selected from the group consisting of silver and gold onto said surface;

directing said vaporized stream of polyphenyl ether onto said surface under temperature conditions sufficient to condense said precursor molecules onto said surface, thereby forming a diamond-like carbon precursor film; and bombarding said diamond-like carbon precursor film with an energetic beam of ions under conditions effective to form on said surface diamond-like carbon coating comprising an amount of said metal atoms sufficient to impart antimicrobial protection to said implant but insufficient to irritate adjacent tissues after implantation.

14. A process of forming an antimicrobial coating on a surface of a biomaterial comprising:

exposing said surface to a vacuum sufficient to permit a vaporized stream of a metallo-organic compound having vaporization properties similar to diffusion pump fluids to condense onto said surface;

directing onto said surface an initial vaporized stream of said metallo-organic compound under temperature conditions sufficient to condense said metallo-organic compound onto said surface, wherein said metallo-organic compound comprises metal atoms selected from the group consisting of atoms of gold, silver, and a combination thereof;

bombarding said surface with an energetic beam of ions under conditions effective to form an amorphous diamond-like carbon coating on said surface comprising a dispersion of said metal atoms;

wherein said dispersion of said metal atoms in said diamond-like carbon coating is effective to provide gradual, controlled release of said metal from said on coating at a rate effective to impart antimicrobial protection, but insufficient to irritate tissue which comes into contact with said surface.

15. The process of claim 14 wherein said metallo-organic compound comprises silver phthalocyanine.

16. The process of claim 14 wherein said process is repeated until said diamond-like carbon coating has a thickness of between about 1–5 microns.

17. The process of claim 15 wherein said process is repeated until said carbonaceous coating has a thickness of between about 1–5 microns.

18. The process of claim 14 wherein said energy is about 10 keV.

19. The method of claim 14 wherein said vacuum comprises a vacuum chamber evacuated to a pressure of about $10^{-5}$ torr or less.

20. A process of forming an antimicrobial coating on a surface of a medical implant comprising:

exposing said surface to a vacuum sufficient to permit a vaporized stream of a carbon-based diffusion pump fluid other than an organosilicon to condense onto said surface of said medical implant;

depositing onto said surface metal atoms selected from the group consisting of silver, gold, and a combination thereof;

directing onto said surface a vaporized stream of said carbon-based diffusion pump fluid under temperature conditions sufficient to condense said fluid onto said surface to form a diamond-like carbon precursor film;

bombarding said diamond-like carbon precursor film with an energetic beam of ions under conditions effective to form on said surface an amorphous diamond-like carbon coating comprising a dispersion of said metal atoms;

wherein said dispersion of said metal atoms in said diamond-like carbon coating is effective to provide gradual, controlled release of said metal from said on coating at a rate effective to impart antimicrobial protection, but insufficient to irritate tissue which comes into contact with said surface.

21. The method of claim 20 wherein said vacuum comprises a vacuum chamber evacuated to a pressure of about $10^{-5}$ torr or less.

22. A process of forming an antimicrobial coating on a surface of a medical implant comprising:

exposing said surface to a vacuum sufficient to permit a vaporized stream of a carbon-based diffusion pump fluid to condense onto a surface of said implant;

subsequently depositing onto said surface metal atoms selected from the group consisting of silver, gold, and a combination thereof;

thereafter directing onto said surface a vaporized stream of said carbon-based diffusion pump fluid under temperature conditions sufficient to condense said fluid onto said surface to form a diamond-like carbon precursor film; and subsequently bombarding said diamond-like carbon precursor film with an energetic beam of ions under conditions effective to form on said surface an amorphous diamond-like carbon coating comprising a dispersion of said metal atoms;

wherein said dispersion of said metal atoms in said diamond-like carbon coating is effective to provide gradual, controlled release of said metal from said on coating at a rate effective to impart antimicrobial protection, but insufficient to irritate tissue which comes into contact with said surface.

23. The method of claim 22 wherein said vacuum comprises a vacuum chamber evacuated to a pressure of about $10^{-5}$ torr or less.

24. The method of claim 22 wherein said carbon-based diffusion pump fluid comprises a fluid other than an organosilicon.

* * * * *